United States Patent [19]

Sakata et al.

[11] Patent Number: 4,879,383

[45] Date of Patent: Nov. 7, 1989

[54] UREA DERIVATIVES

[75] Inventors: Yoshitsugu Sakata, Otsu; Kazunari Hashidume, Wakayama; Tsutomu Iwata, Kobe; Toyoharu Mukai, Daito; Masaaki Kida, Suita, all of Japan

[73] Assignee: Wako Pure Chemical Industries, Ltd., Osaka, Japan

[21] Appl. No.: 67,050

[22] Filed: Jun. 29, 1987

[30] Foreign Application Priority Data

Jul. 1, 1986 [JP] Japan .................................. 61-155872

[51] Int. Cl.$^4$ ................... C07D 265/38; C07D 279/30
[52] U.S. Cl. ....................................... 544/37; 544/103; 546/231; 549/426; 560/27; 562/439; 562/48; 564/39; 564/42; 564/45
[58] Field of Search ................................... 544/37, 103

[56] References Cited

U.S. PATENT DOCUMENTS 3,873,340 3/1975 Miyazawa et al. ................ 544/37 X

FOREIGN PATENT DOCUMENTS 0038205 10/1981
0045220 2/1982
0124287 11/1984

Primary Examiner—Richard L. Raymond
Attorney, Agent, or Firm—Armstrong, Nikaido, Marmelstein, Kubovcik & Murray

[57] ABSTRACT

Urea derivatives of the formula:

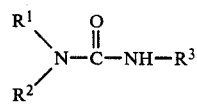

wherein $R^1$ and $R^2$ are independently a 4-disubstituted aminoaryl group or the like, and $R^3$ is a carboxyalkyl group or the like, is soluble in water and effective as a color producing reagent for determining hydrogen peroxide or the like or the activity of peroxidase.

4 Claims, 1 Drawing Sheet

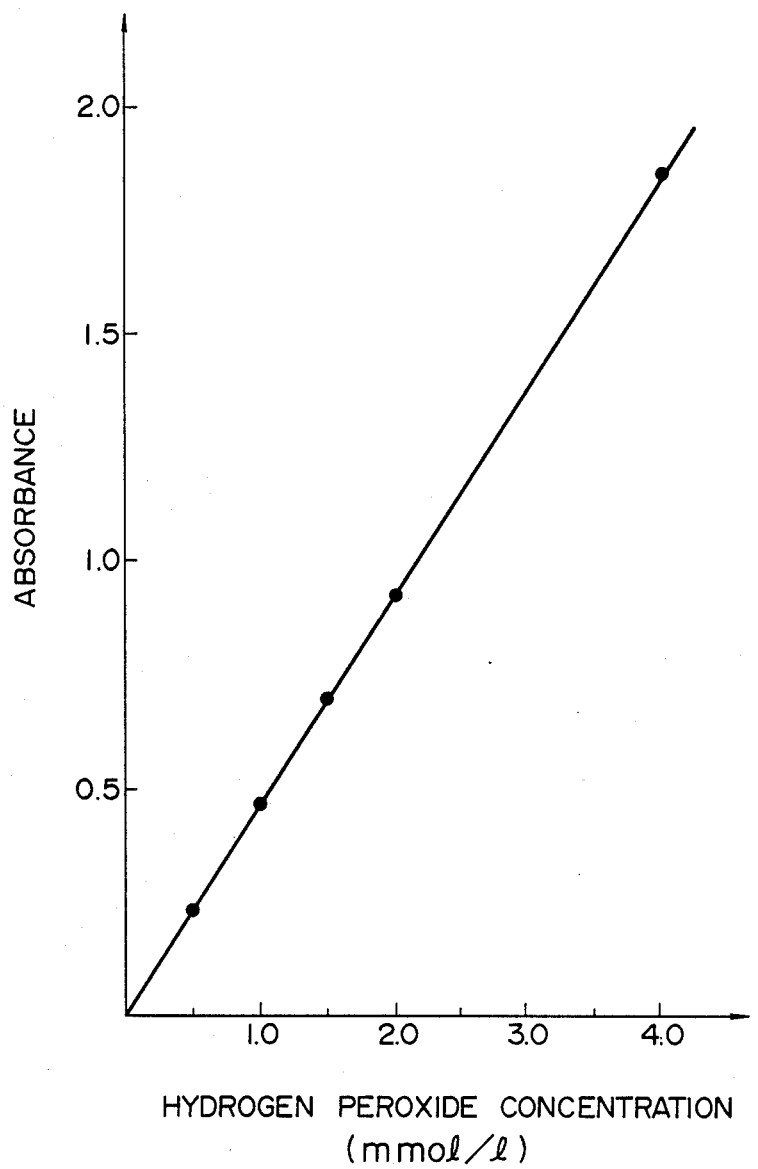

UREA DERIVATIVES

BACKGROUND OF THE INVENTION

This invention relates to a urea derivative and a method for colorimetric determination of an oxidizing substance or a peroxidase-like substance using said urea derivative as a chromogen.

Measurement of living body components, for example, body fluid components such as blood, urine, etc., is essential for the diagnosis of diseases, the elucidation of the state of diseases and course of remedy, since the change or the amount in the living body components is largely related to the diseases. Thus, there have been developed many methods for measuring various kinds of trace components such as cholesterol, triglyceride, glucose, uric acid, phospholipids, bile acids, monoamine oxidase, and the like in blood. It is well known that these methods are useful for the diagnosis of diseases.

As methods for measuring serum components, there are widely employed in general so-called "enzymatic methods" comprising using an enzyme which acts on the desired component specifically when the desired component is other than enzymes, or using a substrate compound when the desired component is an enzyme, conducting an enzymatic reaction respectively, and measuring the product to obtain the amount of the desired component. Among these methods, with the development of oxidizable color producing reagents, there is employed increasingly a method wherein a hydrogen peroxide producing enzyme, for example, an oxidase is used so as to produce $H_2O_2$ corresponding to the desired component, the produced $H_2O_2$ is led to a color forming system by using peroxidase and an oxidizable color producing reagent which is a chromogen, and the color produced is determined colorimetrically to obtain the amount of the desired component. For example, $H_2O_2$ produced by a combination of cholesterol-cholesterol oxidase, triglyceride-lipoprotein lipase-glycerol oxidase, or uric acid-uricase, is led to a color forming system by using peroxidase (POD) and an oxidizable color producing reagent, and absorbance of the color produced is measured to determined the amount of the desired component. Typical examples of the oxidizable color producing reagents which are chromogens used in this method are combined reagents of 4aminoantipyrine and a phenolic compound or an N,N-disubstituted aniline series compound, combined reagents of 3-methylbenzothiazolinone hydrozone (MBTH) and an aniline series compound, 2,2'-azinobis(3-ethylbenzothiazoline-6-sulfonic acid) (ABTS), triphenylmethane series leuco dyes, benzidine derivatives, o-tolidine derivatives, triallylimidazole derivatives, o-phenylenediamine, etc. But almost all the oxidizable color producing reagents have a wavelength of color formed at 600 nm or less and are readily influenced by serum components such as bilirubin, hemoglobin, etc. (in the case of measuring urine components, these are readily influenced by colored matters in urine). Further, chromogens of the oxidizable color producing reagents are low in stability except for the combined reagents of 4-aminoantipyrine and a part of the triphenylmethane series leuco dyes.

On the other hand, there are proposed diphenylamine derivatives which are dye precursors (leuco dyes) and are chromogens relatively good in stability and having a wavelength of color formed at a relatively longer wavelength side in European patent publications Nos. 38205, 124287 and 45220. These diphenylamine derivatives have the wavelength of color formed at a relative longer wavelength side such as 700 nm or more and are relatively high in sensitivity, but are insufficient in chromogen stability and stability of the color formed and poor in solubility in water.

In order to overcome the disadvantages of the diphenylamine derivatives, surface active agents and/or organic solvents are generally used as a dissolution auxiliary so as to make the chromogen soluble and to prepare a color producing reagent solution. But when enzymes such as glycerophosphate oxidase, lipopretein lipase, cholesterol oxidase, cholesterol esterase, phospholipase D, etc. are present in the measuring system, there are many problems, for example, in that these enzymes are relatively easily deactivated by surface active agents and require limited kinds of or concentrations of surface active agents. Therefore, such a process is not preferable. On the other hand, when these diphenylamine derivatives are used as a chromogen in a color producing reagent solution contained in commercially available clinical examination reagents, they have to be contained in socalled lyophilized products, since they have no stability in an aqueous solution for a long period of time. But since the chromogen should be dissolved in a starting liquid of the lyophilized products in amounts 10 to 100 times as much as the concentration usually used, a special technique is required for preparing the starting liquid. Thus, there are many problems in practical use.

SUMMARY OF THE INVENTION

It is an object of this invention to provide a urea derivative which has a maximum absorption wavelength at color development at a longer wavelength side of 650 nm or more and up to the near infrared region, has high sensitivity, and is excellent in both stability of chromogen and stability of color formed, and remarkably high in water solubility. It is another object of this invention to provide a process for measuring the amount of an oxidizing substance or the activity of a peroxidaselike substance by using the urea derivative as a color forming component.

This invention provides a urea derivative represented by the formula:

(I)

wherein $R^1$ and $R^2$ are independently a 4-disubstituted aminoaryl group, and the aryl groups of $R^1$ and $R^2$ may be bonded via an oxygen atom or a sulfur atom; and $R^3$ is a carboxyalkyl group, an alkoxycarbonyl group, an alkylcarbonyl group, an arylsulfonyl group, a sulfoaryl group or a carboxyaryl group.

This invention also provides a process for determining the amount of an oxidizing substance in a sample by using the urea derivative of the formula (I) as a color forming component.

This invention further provides a process for determining the activity of a substance having peroxidase activity in a sample by using the urea derivative of the formula (I) as a color forming component.

BRIEF DESCRIPTION OF THE DRAWING

The attached drawing is a graph showing a calibration curve obtained in Example 6.

DESCRIPTION OF THE PREFERRED EMBODIMENTS

The urea derivative of this invention is represented by the formula:

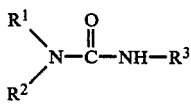
 (I)

wherein $R^1$ and $R^2$ are independently a 4-disubstituted aminoaryl group, and the aryl groups of $R^1$ and $R^2$ may be bonded via an oxygen atom or a sulfur atom; and $R^3$ is a carboxyalkyl group, an alkoxycarbonyl group, an alkylcarbonyl group, an arylsulfonyl group, a sulfoaryl group or a carboxyaryl group, is excellent in stability of chromogen and stability of color formed, thus overcoming the problems of the diphenylamine derivatives, and can be dissolved in water or a buffer solution without using a dissolving auxiliary such as a surface active agent or an organic solvent.

In the urea derivative of the formula (I), the disubstituted amino group in the 4-disubstituted aminoaryl group in the definitions of $R^1$ and $R^2$ can be represented by the formula:

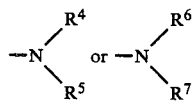

wherein $R^4$, $R^5$, $R^6$ and $R^7$ are independently an alkyl group, a carboxyalkyl group, a hydroxyalkyl group, or an alkoxyalkyl group; the alkyl group moiety in the alkyl group or the substituted alkyl groups is preferably a straight-chain or branched-chain lower alkyl group having 1 to 6 carbon atoms, such as a methyl group, an ethyl group, a propyl group, a butyl group, an amyl group, a hexyl group, etc.; and the alkoxy group moiety in the alkoxyalkyl group is preferably a straight-chain or branched-chain lower alkoxy group having 1 to 6 carbon atoms, such as a methoxy group, an ethoxy group, a propoxy group, a butoxy group, an amyloxy group, a hexyloxy group, etc. Further, the carboxyl group moiety in the carboxyalkyl group may be in the form of a salt such as a salt of an alkali metal, e.g., sodium, potassium, lithium, or the like, or an ammonium salt. $R^4$, $R^5$, $R^6$ and $R^7$ may be the same or different. $R^4$ and $R^5$, and/or $R^6$ and $R^7$ may be bonded to form a ring, and $R^4$, $R^5$ and N, and/or $R^6$, $R^7$ and N, may be bonded to form a ring such as a piperidine ring. The aryl group moiety in the 4-disubstituted aminoaryl group is preferably a phenyl group, a substituted phenyl group (e.g., a tolyl group, a methoxyphenyl group, etc.), a naphthyl group, a substituted naphthyl group (e.g., a methylnaphthyl group, a methoxynaphthyl group, etc.). The aryl groups of $R^1$ and $R^2$ may be bonded via an oxygen atom or a sulfur atom to form a moiety of the formula:

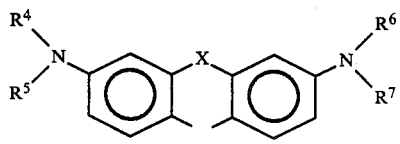

wherein X is S or O.

The alkyl group moiety in the carboxyalkyl group and the alkylcarbonyl group in the definition of $R^3$ is preferably a straight-chain or branched-chain alkyl group having 1 to 6 carbon atoms, such as a methyl group, an ethyl group, a propyl group, a butyl group, an amyl group, a hexyl group, etc. The alkoxy group moiety in the alkoxycarbonyl group is preferably a straight-chain or branched-chain alkoxy group having 1 to 6 carbon atoms, such as a methoxy group, an ethoxy group, a propoxy group, a butoxy group, an amyloxy group, a hexyloxy group, etc. The aryl group moiety in the arylsulfonyl group, the sulfoaryl group and the carboxyaryl group in the definition of $R^3$ is preferably a phenyl group, a substituted phenyl group (e.g., a tolyl group, a methoxyphenyl group), a naphthyl group, a substituted naphthyl group (e.g., a methylnaphthyl group, a methoxynaphthyl group), etc. As $R^3$, the carboxyalkyl group, the alkoxycarbonyl group, the alkylcarbonyl group, the arylsulfonyl group, the sulfoaryl group and the carboxyaryl group are generally used preferably, but not limited thereto. It is also possible to introduce as $R^3$ a functional group having a hydrophilic group, or a functional group having a high polarity structure.

The urea derivative of the formula (I) can be synthesized by reacting a diarylamine derivative of the formula:

 (II)

wherein $R^1$ and $R^2$ are as defined above, with an isocyanate derivative of the formula:

 (III)

wherein $R^8$ is a carboxyalkyl group, an alkoxycarbonyl group, an alkylcarbonyl group, an arylsulfonyl group, a sulfoaryl group, a carboxyaryl group or an alkoxycarbonylalkyl group, in almost equimolar amounts in a suitable organic solvent such as chloroform, n-hexane, ethyl acetate, dimethylformamide, etc., at a temperature of usually 10° C. to 100° C., preferably 20° C. to 90° C., for a few to several tens hours.

After the reaction, the desired urea derivative of the formula (I) can be obtained by a conventional after treatment such as isolation and purification by e.g. column chromatography, or if necessary by an alkali treatment (e.g. in the case of $R^8$ being an alkoxycarbonylalkyl group), followed by the conventional aftertreatment mentioned above.

The diarylamine derivative of the formula (II) can be produced according to a well-known indamine production process [e.g. Chem. Ber., 16, 464 (1883)] by reacting, for example, an aniline derivative with a phenylenediamine derivative in the presence of periodic acid for oxidative condensation to form a dye, which is then reduced.

The isocyanate derivative of the formula (III) can be synthesized according to a process for producing an isocyanate described in, for example, Organic Chemistry vol. 5, pp 452–453, published by Asakura Shoten Ltd. 6th ed. (1967).

The urea derivative of the formula (I) is very stable in water or an aqueous solution dissolving a surface active agent, and has a low blank value. When the urea derivative of the formula (I) is oxidized by hydrogen peroxide in the presence of an oxidizing agent such as peroxidase, there can be quantitatively formed a dye having a maximum absorption in the range from 650 nm to near infrared region and being excellent in stability of color formed. Since the urea derivative of the formula (I) has a hydrophilic functional group or a highly polar structure, it is very good in solubility in water or an aqueous solution dissolving a surface active agent. Therefore, it can advantageously be used for preparing a color producing reagent solution.

Various properties such as the stability of leuco dye solution, the stability after color developed, the maximum absorption wavelength ($\lambda$max), the sensitivity ($\epsilon$) and the solubility in water of typical 14 examples of the urea derivatives of the formula (I) are shown in Table 1.

In Table 1, "A" means stable and "B" means slightly unstable in the evaluation of the stability of the leuco dye solution and the stability after color development. The solubility in water is evaluated as ⊙ highly soluble, ○ soluble, and X hardly soluble.

TABLE 1

| Compound No. | R₁ | R₂ | R₃ | Stability of leuco dye soln. | Stability after color developed | $\lambda max/min$ ($\varepsilon$) | Solubility in water |
|---|---|---|---|---|---|---|---|
| Compound of this invention (1) | 4-methylphenyl-N(CH₃)₂ | 4-methylphenyl-N(CH₃)₂ | $-CH_2-\overset{O}{\underset{\|}{C}}-ONa$ | A | B | 730 ($9 \times 10^4$) | |
| (2) | 4-methylphenyl-N(CH₃)₂ | 4-methylphenyl-N(CH₃)₂ | 4-methylphenyl-SO₃Na | A | B | 730 ($9 \times 10^4$) | |
| (3) | 3-methyl-4-methylphenyl-N(C₂H₄OC₄H₉)₂ | 3-methyl-4-methylphenyl-N(C₅H₁₁)₂ | $-CH_2-\overset{O}{\underset{\|}{C}}-ONa$ | A | A | 755 ($8 \times 10^4$) | |
| (4) | 4-methylphenyl-N(C₂H₄OC₄H₉)₂ | 3-methyl-4-methylphenyl-N(C₅H₁₁)₂ | $-CH_2-\overset{O}{\underset{\|}{C}}-ONa$ | A | A | 750 ($8 \times 10^4$) | |
| (5) | 4-methylphenyl-N(CH₂OH)(CH₃) | 4-methylphenyl-piperidinyl | 4-(methylsulfonyl)phenyl-CH₃ | A | B | 730 ($9 \times 10^4$) | |
| (6) | 4-methylphenyl-N(CH₂OH)(CH₃) | 4-methylphenyl-N(CH₃)₂ | tetrahydropyran-4-yl-C₂H₄ | A | B | 730 ($9 \times 10^4$) | |
| (7) | 3-methyl-4-methylphenyl-N(C₂H₅)₂ | 3-methyl-4-methylphenyl-N(CH₃)₂ | 4-(methylsulfonyl)phenyl-CH₃ | A | A | 740 ($7 \times 10^4$) | |

TABLE 1-continued

| Compound No. | R₁ | R₂ | R₃ | Stability of leuco dye soln. | Stability after color developed | λmax/min (ε) | Solubility in water |
|---|---|---|---|---|---|---|---|
| (8) | 3-methyl-4-methylphenyl-N(C₂H₄OH)₂ | 3-methyl-4-methylphenyl-N(CH₃)₂ | 4-(methylsulfonyl)phenyl | A | A | 745 (7 × 10⁴) | |
| (9) | (CH₃)₂N-substituted thianthrene | phenyl-N(CH₃)₂ | —CH₂—C(O)—ONa | B | B | 666 (9 × 10⁴) | |
| (10) | (CH₃)₂N-substituted dibenzofuran | phenyl-N(CH₃)₂ | —CH₂—C(O)—ONa | B | B | 666 (9 × 10⁴) | |
| (11) | (C₃H₇)₂N-substituted dibenzofuran | phenyl-N(C₃H₇)₂ | —CH₂—C(O)—ONa | A | B | 666 (9 × 10⁴) | |
| (12) | (C₃H₇)₂N-substituted thianthrene | phenyl-N(C₃H₇)₂ | —CH₂—C(O)—ONa | A | B | 666 (9 × 10⁴) | |
| (13) | (CH₃)₂N-substituted dibenzofuran | phenyl-N(CH₃)(CH₂COONa) | —CH₂—C(O)—ONa | B | B | 666 (9 × 10⁴) | |
| (14) | (CH₃)₂N-substituted thianthrene | phenyl-N(CH₃)(CH₂COONa) | —CH₂—C(O)—ONa | B | B | 666 (9 × 10⁴) | |

Known compound

TABLE 1-continued
| Compound No. | R₁ | R₂ | R₃ | Stability of leuco dye soln. | Stability after color developed | λmax/min (ε) | Solubility in water |
|---|---|---|---|---|---|---|---|
| (15) | 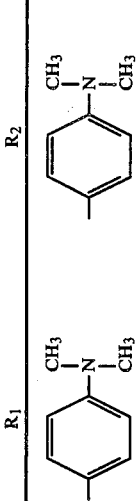 | 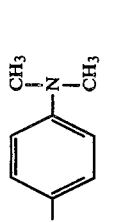 | —CH₃ | A | B | 730 (8 × 10⁴) | x |
| (16) | 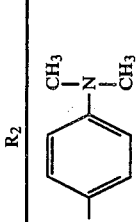 | 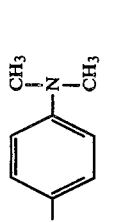 | —C₄H₉ | A | B | 730 (8 × 10⁴) | x |
| (17) | 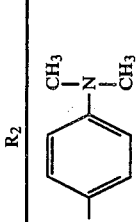 | | —CH₃ | B | B | 666 (9 × 10⁴) | x |

The urea derivative of the formula (I) can effectively be used as a color forming component for determining the oxidizing substance or for determining the activity of a peroxidase-like substance. The term "oxidizing substance" means hydrogen peroxide, periodic acid and an alkali metal salt thereof, perboric acid and an alkali metal salt thereof, iodic acid and an alkali metal salt thereof. Particularly, the urea derivative of the formula (I) can effectively be used as a color forming component in the determination of trace components in a living body sample wherein hydrogen peroxide produced by an enzymatic reaction is led to a color forming system in the presence of peroxidase, and the color produced is determined colorimetrically.

That is, the determination of the oxidizing substance can be applied to the determination of living body components and can be carried out by causing an oxidase to react on a substrate or a substance produced by an enzymatic reaction, and measuring the amount of hydrogen peroxide. Such a method is particularly effective for determining the amount of substrates or the activity of enzymes present in living body samples as trace components.

Examples of the trace components present in living body samples measurable by the process of this invention are substrates such as cholesterol, glucose, glycerin, triglyceride, non-esterified fatty acids, uric acid, phospholipids, bile acids, creatine, etc. and enzymes such as monoamine oxidase, guanase, choline esterase, amylase, transaminases, e.g. glutamic-pyruvic transaminase, glutamic-oxaloacetic transaminase, etc. Other living body components measurable by determining hydrogen peroxide produced by conventional enzymatic reactions can be determined by the process of this invention.

The determination process of this invention can be carried out by a conventional enzymatic method (using a hydrogen peroxide producing enzyme) except for using the urea derivative of the formula (I) as a color producing agent (an oxidizable color producing reagent).

The amount of the color producing agent used in the process of this invention is usually 4 to 5 $\mu$mol/l or more, preferably 50 to 100 $\mu$mol/l.

In the above-mentioned determination of living body components, the kinds and amounts of the oxidase (which is used as an enzyme for producing hydrogen peroxide) and other enzymes used for other purposes, substrates which pertain to the enzymatic reaction and other substances, can be determined or selected properly according to known determination methods of living body components using known oxidizable color producing reagents and depending on the substance to be measured.

As the peroxidase used in the determination of hydrogen peroxide, there can be used those derived from plants, animals, and microorganisms and peroxidase-like substances alone or as a mixture thereof. The amount of the peroxidase is preferably 0.01-10 units/ml and may be changed depending on purposes.

The determination of living body components can be carried out preferably at a pH of 4.0 to 10.0, more preferably at a pH of 6.0 to 8.0. As the buffering agent, there can be used a phosphate buffer, a citrate buffer, a borate buffer, a carbonate buffer, a tris buffer, a Good's buffer, and the like.

The urea derivative of the formula (I) can also be used for determining the activity of a peroxidase-like substances in the presence of hydrogen peroxide. The term "peroxidase-like substance" means a substance having peroxidase activity, e.g. peroxidase itself, a heme compound such as hemoglobin and the like.

Further, the urea derivative of the formula (I) can also be used for enzyme immunoassay using peroxidase as a labeled compound. Further, it can also be used for measuring the hemoglobin in serum by using an oxidizing substance such as hydrogen peroxide or sodium perborate.

More concretely, the trace components present in living body samples can be measured as follows:

(1) Cholesterol (Reactions)

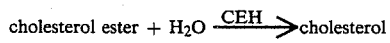

cholesterol ester + H$_2$O $\xrightarrow{\text{CEH}}$ cholesterol

cholesterol + O$_2$ $\xrightarrow{\text{COD}}$ $\Delta^4$ − cholestenone + H$_2$O$_2$

H$_2$O$_2$ + urea derivative $\xrightarrow{\text{POD}}$ color development (Reagent solution)
0.1 M tris-maleate buffer (pH 7.0)

| | | |
|---|---|---|
| cholesterol esterase (CEH) | 0.1–10 u/ml | (0.3 u/ml) |
| cholesterol oxidase (COD) | 0.1–10 u/ml | (0.4 u/ml) |
| peroxidase (POD) | 0.3–30 u/ml | (5 u/ml) |
| Triton X-100 | 0.05–0.2% | (0.1%) |
| urea derivative | 40–200 $\mu$M | (100 $\mu$M) |
| ascorbate oxidase | 3–20 u/ml | (5 u/ml) |

(Procedure)

Sample + Reagent solution $\xrightarrow{\text{(incubate)}}$ color development
(10 $\mu$l)    (3 ml)                            (measurement)

(1') Free cholesterol
(Reactions)

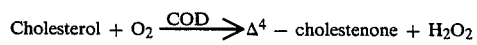

Cholesterol + O$_2$ $\xrightarrow{\text{COD}}$ $\Delta^4$ − cholestenone + H$_2$O$_2$ -continued H$_2$O$_2$ + urea derivative $\xrightarrow{POD}$ color development (Reagent solution)
The same as mentioned above
(Procedure)
The same as mentioned above (2) Glucose
(Reactions)

glucose + O$_2$ + H$_2$O $\xrightarrow{GOD}$ H$_2$O$_2$ + gluconic acid

H$_2$O$_2$ + urea derivative $\xrightarrow{POD}$ color development (Reagent solution)
0.1 M phosphate buffer (pH 7.0)

| | | |
|---|---|---|
| glucose oxidase (GOD) | 10–100 u/ml | (30 u/ml) |
| peroxidase (POD) | 0.3–30 u/ml | (5 u/ml) |
| urea derivative | 50–300 μM | (100 μM) |
| [mutarotase | 0.02–0.5 u/ml | (0.067 u/ml)] |
| ascorbate oxidase (AOD) | 3–20 u/ml | (5 u/ml) |

(Procedure)

Sample + Reagent solution $\xrightarrow{\text{(incubate)}}$ color development (measurement)
(10 μl)    (3 ml)

(3) Triglyceride
(Reactions)

triglyceride + 3H$_2$O $\xrightarrow{LPL}$ glycerol + 3 fatty acids glycerol + ATP $\xrightarrow{GK}$ glycerol-3-phosphate + ADP glycerol-3-phosphate + O$_2$ $\xrightarrow{GPO}$ dihydroxyacetone phosphate + H$_2$O$_2$ H$_2$O$_2$ + urea derivative $\xrightarrow{POD}$ color development (Reagent solution)
tris buffer (pH 6.5)

| | | |
|---|---|---|
| glycerol kinase (GK) | 0.5–15 u/ml | (5 u/ml) |
| glycerol-3-phosphate oxidase (GPO) | 1–20 u/ml | (5 u/ml) |
| peroxidase (POD) | 0.3–30 u/ml | (5 u/ml) |
| magnesium acetate | 1–7 mM | (2 mM) |
| adenosine-5′-triphosphate | 0.5–30 mM | (2 mM) |
| lipoprotein lipase (LPL) | 10–150 u/ml | (60 u/ml) |
| urea derivative | 50–300 μM | (100 μM) |
| ascorbate oxidase (AOD) | 3–20 u/ml | (5 u/ml) |

(Procedure)

Sample + Reagent solution $\xrightarrow{\text{(incubate)}}$ color development (measurement)
(10 μl)    (3 ml)

(3′) Glycerol
(Reactions)

glycerol + ATP $\xrightarrow{GK}$ glycerol-3-phosphate + ADP glycerol-3-phosphate + O$_2$ $\xrightarrow{GPO}$ dihydroxyacetone phosphate + H$_2$O$_2$ H$_2$O$_2$ + urea derivative $\xrightarrow{POD}$ color development (Reagent solution)
The same as mentioned above
(Procedure)
The same as mentioned above (4) Non-esterified fatty acid
(Reactions)

RCOOH + ATP + CoA $\xrightarrow{ACS}$ Acryl-CoA—AMP + PPI

Acryl-CoA + O$_2$ $\xrightarrow{\text{ACOD}}$ 2,3-trans-Enoyl-CoA + H$_2$O$_2$

H$_2$O$_2$ + urea derivative $\xrightarrow{\text{POD}}$ color development (Reagent solution)
PIPES-NaOH buffer (pH 6.9)

| | | |
|---|---|---|
| acryl coenzyme A synthesizer (ACS) | 0.05–5 u/ml | (0.1 u/ml) |
| acryl coenzyme A oxidase (ACOD) | 1–15 u/ml | (3 u/ml) |
| coenzyme A (CoA) | 0.2–5 mg/ml | (0.5 mg/ml) |
| Peroxidase (POD) | 0.3–30 u/ml | (5 u/ml) |
| ascorbate oxidase (AOD) | 3–20 u/ml | (5 u/ml) |
| adenosine-5'-phosphate (ATP) | 1–15 mg/ml | (3 mg/ml) |
| magnesium chloride | 0.5–5 mM | (2 mM) |
| Emulgen 913 (polyoxyethylene nonyl phenol ether) | 0.05–0.4% | (0.2%) |

(Procedure)

Sample + Reagent solution $\xrightarrow{\text{(incubate)}}$ color development
(20 μl)   (3 ml)     (measurement)

(5) Uric acid
(Reactions)

uric acid + O$_2$ + 2H$_2$O $\xrightarrow{\text{uricase}}$ allantoin + CO$_2$ + H$_2$O$_2$ H$_2$O$_2$ + urea derivative $\xrightarrow{\text{POD}}$ color development (Reagent solution)
PIPES-NaOH buffer (pH 6.4)

| | | |
|---|---|---|
| uricase | 0.5–10 u/ml | (2 u/ml) |
| peroxidase (POD) | 0.3–30 u/ml | (10 u/ml) |
| ascorbate oxidase (AOD) | 1–20 u/ml | (2 u/ml) |
| urea derivative | 20–300 μM | (50 μM) |

(procedure)

Sample + Reagent solution $\xrightarrow{\text{(incubate)}}$ color development
(10 μl)   (3 ml)     (measurement)

(6) Phospholipids
(Reactions)

phospholipids $\begin{pmatrix} \text{lecithin} \\ \text{sphingosine} \\ \text{lysolecithin} \end{pmatrix}$ + H$_2$O $\xrightarrow{\text{phospholipids}}$ choline + $\begin{pmatrix} \text{phosphatidic acid} \\ \text{N—acylsphingosyl phosphate} \\ \text{lysophosphatidic acid} \end{pmatrix}$ choline $\xrightarrow{\text{choline oxidase}}$ betaine + 2H$_2$O H$_2$O$_2$ + urea derivative $\xrightarrow{\text{POD}}$ color development (Reagent solution)
tris buffer (pH 7.7)

| | | |
|---|---|---|
| phospholipase D | 0.4–10 u/ml | (0.7 u/ml) |
| choline oxidase | 1–20 u/ml | (3 u/ml) |
| peroxidase (POD) | 0.3–30 u/ml | (5 u/ml) |
| ascorbate oxidase | 2–20 u/ml | (5 u/ml) |
| urea derivative | 50–300 μM | (100 μM) |

(Procedure)

Sample + Reagent solution $\xrightarrow{\text{(incubate)}}$ color development
(10 μl)   (3 ml)     (measurement)

(7) Monoamine oxidase (MAO)
(Reactions)

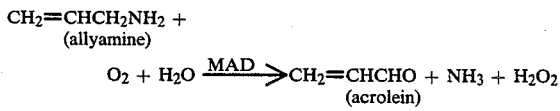

H$_2$O$_2$ + urea derivative $\xrightarrow{POD}$ color development (Reagent solution)
25 mM PIPES-NaOH buffer (pH 6.75)

| | | |
|---|---|---|
| allylamine | 10–100 mM | (25 mM) |
| peroxidase (POD) | 0.3–30 u/ml | (5 u/ml) |
| ascorbate oxidase | 2–20 u/ml | (5 u/ml) |
| urea derivative | 5–100 μM | (30 μM) |

(Procedure)

Sample + Reagent Solution $\longrightarrow$ rate assay
(100 μl)    (3 ml)    (incubate)

(8) Transaminase
(A) Glutamic oxaloacetic transaminase (GOT)
L-aspartic acid +

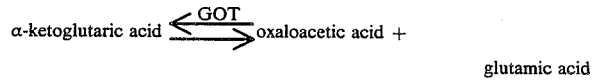
glutamic acid oxaloacetic acid $\xrightarrow{OAC}$ pyruvic acid + CO$_2$ (B) Glutamic pyruvic transaminase

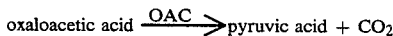
glutamic acid pyruvic acid + HOPO$_3^{2-}$ O$_2$ $\xrightarrow{POP}$ acetyl phosphate + CO$_2$ + H$_2$O$_2$ H$_2$O$_2$ + urea derivative $\xrightarrow{POD}$ color development (Reagent solution)
(A) GPT
First solution:
phosphate buffer (pH 7.0)

| | | |
|---|---|---|
| pyruvate oxidase (POP) | 1–10 u/ml | (6 u/ml) |
| peroxidase (POD) | 0.2–20 u/ml | (10 u/ml) |
| thiamine pyrophosphate (TPP) | 0.01–0.5% | (0.06%) |
| flavin-adenine dinucleotide (FAD) | 0.001–0.1% | (0.002%) |
| magnesium acetate | 1–10 mM | (9 mM) |
| catalase | 50–500 u/ml | (100 u/ml) |

Second solution:
phosphate buffer (pH 7.0)

| | | |
|---|---|---|
| DL-alanine | 200–800 mM | (700 mM) |
| α-ketoglutamic acid | 10–50 mM | (35 mM) |
| urea derivative | 20–300 μM | (50 μM) |
| NaN$_3$ | 0.1–0.4% | (0.2%) |

Third solution (Reaction stopper):
0.1 M citrate buffer (pH 6.8)

| | | |
|---|---|---|
| sodium dodecylbenzenesulfonate | 0.1–1% | (0.5%) |
| EDTA.2Na | 0.5–2 mM/l | (1 mM/l) |

(procedure)

Sample + 1st reagent $\xrightarrow[\text{(37° C., 5 min)}]{\text{(incubate)}}$ + 2nd reagent $\xrightarrow[\text{(37° C., 20 min)}]{\text{incubate}}$ +
(20 μl)    solution                                   solution
         (0.5 ml)                                    (0.5 ml)

reaction stopper $\longrightarrow$ color development
(2 ml)                    (measurement)

(B) GOT
First solution:
Phosphate buffer (pH 7.0)

| | | |
|---|---|---|
| pyruvate oxidase (POP) | 1–10 u/ml | (6 u/ml) |
| peroxidase (POD) | 0.2–20 u/ml | (10 u/ml) |
| thiamine pyrophosphate (TPP) | 0.01–0.5% | (0.06%) |
| flavin-adenine dinucleotide (FAD) | 0.001–0.1% | (0.002%) |
| magnesium acetate | 1–10 mM | (9 mM) |
| catalase | 50–500 u/ml | (100 u/ml) |
| oxaloacetate decarboxylase | 1–50 u/ml | (20 u/ml) |
| | 1–50 u/ml | (20 u/ml) |

Second solution:
phosphate buffer (pH 7.0)

| | | |
|---|---|---|
| L-aspartic acid | 100–600 mM | (400 mM) |
| α-ketoglutaric acid | 10–50 mM | (35 mM) |
| urea derivative | 20–300 μM | (50 μM) |
| NaN₃ | 0.1–0.4% | (0.2%) |

Third solution (Reaction Stopper):
0.1 M citrate buffer (pH 6.8)

| | | |
|---|---|---|
| sodium dodecyl-benzenesulfonate | 0.1–1% | (0.5%) |
| EDTA·2Na | 0.5–2 mM/l | (1 mM/l) |

(Procedure)

Sample + 1st reagent $\xrightarrow{\text{(incubate)}}_{(37°\text{C., 5 min})}$ + 2nd reagent $\xrightarrow{\text{(incubate)}}_{(37°\text{C., 20 min})}$ +
(20 μl)   solution                                 solution
          (0.5 ml)                                 (0.5 ml)

reaction stopper ⟶ color development
(2 ml)

(9) Creatine
(Reactions)

creatine + H₂O $\xrightarrow{\text{creatine amidinohydrase}}$ sarcosine + urea sarcosine + H₂O + O₂ $\xrightarrow{\text{sarcosine oxidase}}$ H₂O₂ + HCHO + glycine H₂O₂ + urea derivative $\xrightarrow{\text{POD}}$ color development (Reagent solution)
First solution:
50 mM phosphate buffer (pH 8.0)

| | | |
|---|---|---|
| sarcosine oxidase | 1–40 u/ml | (20 u/ml) |
| peroxidase | 0.2–20 u/ml | (10 u/ml) |
| catalase | 50–400 u/ml | (100 u/ml) |

Second solution:
50 mM phosphate buffer (pH 8.0)

| | | |
|---|---|---|
| creatine amidinohydrase | 1–100 u/ml | (50 u/ml) |
| NaN₃ | 0.1–0.4% | (0.2%) |
| urea derivative | 30–400 μM | (50 μM) |

(Procedure)

Sample + 1st reagent $\xrightarrow{\text{(incubate)}}_{(37°\text{C., 5 min})}$ +
(50 μl)   solution
          (1 ml)

2nd reagent $\xrightarrow{\text{(incubate)}}_{(37°\text{C., 5–10 min})}$ color development (measurement)
solution
(1 ml)

(10) Bile acids
(Reactions)

3α-hydroxysteroid + NAD⁺ $\xrightarrow{\text{3α-HSD}}$ 3-ketosteroid + NADH + H⁺

NADH + urea derivative $\xrightarrow[\text{Mn}^{2+}]{\text{POD}}$ color development (Reagent solution)
50 mM tris-HCl buffer (pH 8.0)

| -continued | | |
|---|---|---|
| 3α-hydroxysteroid dehydrogenase (3α-HSD) | 0.005–1 u/ml | (0.01 u/ml) |
| nicotinamide adenine dinucleotide (NAD) | 0.1–3 mM | (1 mM) |
| MnCl₂ | 0.2–5 mM | (1 mM) |
| peroxidase (POD) | 0.2–30 u/ml | (3 u/ml) |
| urea derivative | 30–300 μM | (50 μM) |

(Procedure)

Sample + Reagent solution →(incubate)(37° C., 20 min)→ color development (measurement)
(50 μl)      (3 ml)

(11) Peroxidase
(Reaction)

urea derivatives + H₂O₂ —POD→ color development
                (substrate)

(Reagent solution)
50 mM phosphate buffer (pH 6.0)
urea derivative         30–300 μM        (50 μM)
H₂O₂                    0.02–0.3 mM      (0.1 mM)

(Procedure)

Sample + Reagent solution →(incubate)→ color developement
(10 μl)      (3 ml)                    (measurement)

The POD activity can be obtained by measuring the changing rate per unit time. This procedure can also be applied to the determination of hemoglobin.

This invention is illustrated by way of the following Examples, but is not limited thereto.

EXAMPLE 1

Synthesis of sodium salt of N,N-bis(4-dimethylaminophenyl)-N'-carboxymethylurea [Compound No. (1) in Table 1]

In 100 ml of chloroform, 2.5 g of Bindshedler's Green, Leuco Base [4,4'-bis(dimethylamino)diphenylamine](mfd. by Dojin Kagaku Kenkyusho, hereinafter referred to as "BG") was dissolved, and 1.3 g of ethyl acetate isocyanate (mfd. by Kanto Kagaku K.K.) was gradually added thereto and reacted at 20° C. for 20 hours. The reaction mixture was applied to a column packed with silica gel of 100 to 200 mesh (solvent: chloroform) and eluted with a mixed solvent of chloroform and methanol to obtain the desired fraction. Then the chloroform and the methanol were removed by distillation. To the residue, 300 ml of methanol and 10 ml of 1N NaOH were added and the reaction was carried out at 20° C. for 10 hours, followed by concentration and lyophilization to give 2.1 g of colorless crystals.

TLC (silica gel, chloroform: methanol=9:1): Rf=0.4
NMR (CDCl₃)(ethyl ester body): δ ppm 1.31 (3H, t, —CH₂CH₃), 2.22 (2H, q, —CH₂CH₃), 2.40 (2H, d, —CH₂—C(=O)—), 3.15 (12H, s, 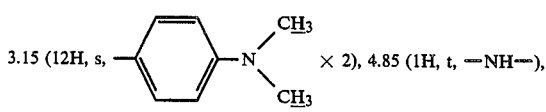 × 2), 4.85 (1H, t, —NH—), 6.65–7.45 (8H, m, aromatic H).

NMR (CDCl₃)(free body): δ ppm 3.15 (12H, s,

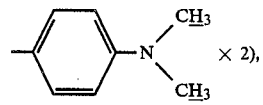 × 2), 3.73 (2H, s, —CH₂), 4.73 (1H, s, —NH—), 6.65–7.48 (8H, m, aromatic H).

MS: M⁺ = 378.

IR: $\nu_{NH}$=3400 cm⁻¹, $\nu_{CH}$=2930 cm⁻¹, $\nu_{C=O}$=1650 cm⁻¹, $\nu_{C-O}$=1100 cm⁻¹.

EXAMPLE 2

Synthesis of sodium salt of N,N-bis(4-dimethylaminophenyl)-N'-(4-sulfophenyl)urea [Compound No. (2) in Table 1]

In 100 ml of dimethylsulfoxide (DMSO), 5 g of BG and 2.55 g of sodium salt of 4-sulfophenyl isocyanate (mfd. by Aldrich Chemical Company) were dissolved and reacted at 80° C. for 20 hours. The reaction mixture was applied to a column packed with silica gel of 100 to 200 mesh (solvent: chloroform) and eluted with a mixed solvent of chloroform and methanol, followed by concentration and drying of the desired fraction to give 150 mg of colorless crystals.

TLC (silica gel, methanol): R_f=0.1
NMR (DMSO-d₆): δ ppm 3.10 (12H, s,

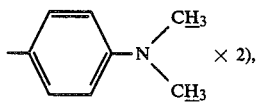 × 2), 6.21–7.40 (12H, m, aromatic H), 4.75 (1H, s, —NH—).

MS: M⁺ =454.

IR: $\nu_{NH}$=3400 cm$^{-1}$, $\nu_{CH}$=2930 cm$^{-1}$, $\nu_{C=O}$=1650 cm$^{-1}$, $\nu_{SO2}$=1200 cm$^{-1}$.

EXAMPLE 3

Synthesis of N-(4-dimethylamino-2-methylphenyl)-N-(4'-diethylamino-2'-methylphenyl)-N'-(4-methylphenylsulfonyl)urea [Compound No. (7) in Table 1]

In 100 ml of methanol, 2.1 g of N,N-diethyltolylenediamine·hydrochloride and 2.4 g of N,N-dimethyl-m-toluidine were dissolved and 3 g of periodic acid was added thereto and reacted at room temperature for 1 hour. Then, 6 g of zinc powder and 5 ml of 6N HCl were added to the reaction mixture and reacted. After the reaction, the reaction mixture was extracted with chloroform. The oil layer was dried over anhydrous magnesium sulfate. Then, 9 g of p-toluenesulfonyl isocyanate was added thereto and the reaction was carried out for 2 hours at room temperature. The reaction mixture was applied to a column packed with silica gel of 100 to 200 mesh (solvent: chloroform, hexane) and eluted with a mixed solvent of chloroform and hexane, followed by concentration and drying of the desired fraction to give 50 mg of colorless crystals.

TLC (silica gel, chloroform: hexane=1:1): $R_f$=0.55
MS: M$^+$=508.
NMR (CDCl$_3$): δ ppm 1.25, 1.16

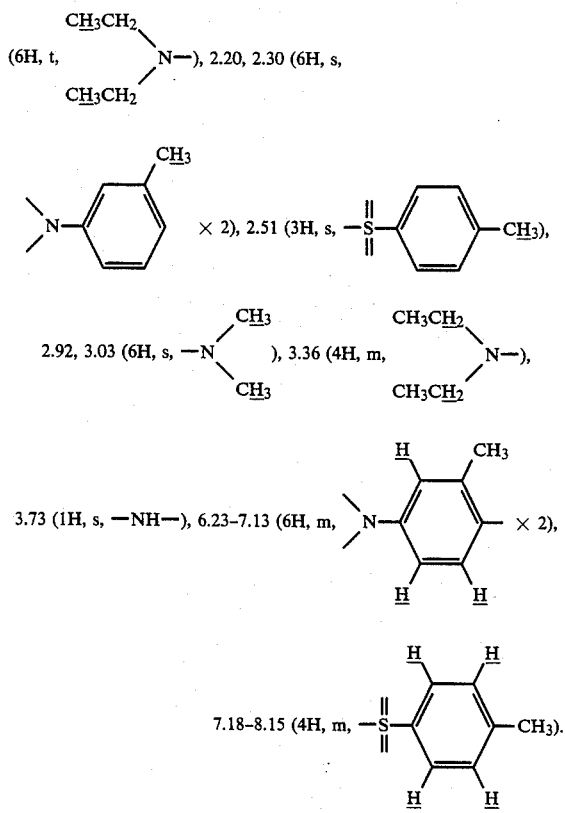

IR (KBr): $\nu_{NH}$=3240 cm$^{-1}$, $\nu$C=O=1695 cm$^{-1}$, $\nu_s$SO$_2$=1350 cm$^{-1}$, $\nu_{as}$SO$_2$=1165 cm$^{-1}$.

EXAMPLE 4

Synthesis of sodium salt of 10-(carboxymethylaminocarbonyl)-3,7-bis(dimethylamino)phenothiazine [Compound No. (9) in Table 1]

In 300 ml of distilled water, 3.0 g of Methylene

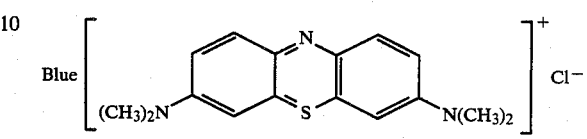

(mfd. by Wako Pure Chemical Industries, Ltd.) was dissolved and reduced by using 3 g of zinc powder and 10 ml of 1N HCl. After removing the zinc, the reaction solution was extracted with ethyl acetate under basic conditions, and the oil layer was dehydrated over anhydrous magnesium sulfate. Subsequently, 2.7 g of ethyl acetate isocyanate (mfd. by Kanto Kagaku K.K.) was added to the reaction solution and the reaction was carried out at room temperature for 20 hours. After concentrating the reaction solution, it was purified by silica gel column chromatography (silica gel: 100–200 mesh, elution solvent: chloroform) to give the desired fraction. From this fraction, the chloroform was removed by distillation, and then 500 ml of methanol and 10 ml of 1N NaOH were added thereto and reacted at 20° C. for 10 hours. After concentration and lyophilization, 980 mg of colorless crystals were obtained.

TLC (silica gel, chloroform: methanol=9:1): $R_f$=0.5.
NMR (DMSO-d$_6$): δ ppm 3.17 (12H, s,

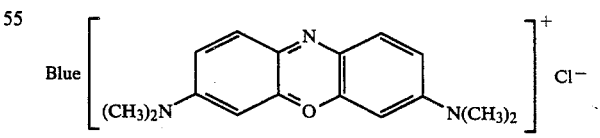

3.74 (2H, s, —CH$_2$-), 4.75 (1H, s, —NH—), 6.72–7.55 (6H, m, aromatic H).
MS: M$^+$=408.
IR: $\nu_{NH}$=3400 $cm^{-1}$, $\nu_{CH}$=2930 cm$^{-1}$, $\nu_{C=O}$=1650 cm$^{-1}$, $\nu_{O-C}$=1100 cm$^{-1}$.

EXAMPLE 5

Synthesis of sodium salt of 10-(carboxymethylaminocarbonyl)-3,7-bis(dimethylamino)phenoxazine [Compound No. (10) in Table 1]

In 300 ml of distilled water, 2.7 g of Capri

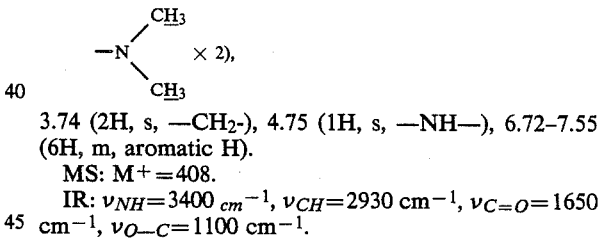

(mfd. by Tokyo Kasei K.K) was dissolved and reduced by using 3 g of zinc powder and 10 ml of 1N HCl. After removing the zinc, the reaction solution was extracted with ethyl acetate under basic conditions. The oil layer wad dehydrated over anhydrous magnesium sulfate. Subsequently 2.7 g of ethyl acetate isocyanate was added to the reaction solution and reacted at room temperature for 20 hours. After concentrating the reaction solution, it was purified by silica gel column chromatography (silica gel: 100–200 mesh, elution solvent: chloroform) to give the desired fraction. From this fraction, the chloroform was removed by distillation, and then 500 ml of methanol and 10 ml of 1N NaOH were added thereto and reacted at 20° C. for 10 hours. After concentraton and lyophilization, 980 mg of colorless crystals were obtained.

TLC (silica gel, chloroform: methanol=9:1): $R_f=0.5$.

NMR (CDCl$_3$)(ethyl ester body): δ ppm 1.35 (3H, t, —CH$_2$CH$_3$), 2.25 (2H, q, —CH$_2$CH$_3$), 2.40 (2H, d, —CH$_2$—), 3.17 (12H, s,

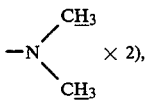

× 2), 4.90 (1H, t, —NH—), 6.72–7.55 (6H, m, aromatic H).
MS: M$^+$=392.
IR: $\nu_{NH}$=3400 cm$^{-1}$, $\nu_{CH}$=2930 cm$^{-1}$, $\nu_{C=O}$=1650 cm$^{-1}$, $\nu_{O-C}$=1100 cm$^{-1}$.

EXAMPLE 6

Determination of Hydrogen Peroxide [Measuring reagent solution]

Compound No. (1) obtained in Example 1 in an amount of 0.05 mmol/l. and 10 U/ml of peroxidase were dissolved in 50 mM PIPES [piperadine-N,N'-bis(2-ethanesulfonic acid)]-sodium hydroxide buffer solution (pH 7.0).

[Sample solution]
Commercially available aqueous hydrogen peroxide was diluted with deionized water so as to make the concentration 0.5, 1.0, 1.5, 2.0 and 4.0 mmol/l.

[Measuring method]
To 3 ml of the measuring reagent solution, 20 μl of a sample solution was added and incubated at 37° C. for 5 minutes. Then, absorbance at 730 nm (OD$_{730}$) was measured.

[Results]
The results are shown in the attached drawing which shows a calibration curve. As is clear from the drawing, the calibration curve obtained by plotting absorbances (OD$_{730}$) corresponding to individual H$_2$O$_2$ concentrations shows good quantitativeness.

EXAMPLE 7

Determination of Hydrogen Peroxide in the Presence of Normal Human Serum
[Measuring reagent solution]
The same as used in Example 6.
[Sample solution]
The same as used in Example 6.
[Measuring method]
To 3 ml of the measuring reagent solution, 50 μl of normal human serum or deionized water was added and then 20 μl of a sample solution was added. After incubating at 37° C. for 5 minutes, absorbance at 730 nm (OD$_{730}$) was measured.
[Results]
A relationship between the hydrogen peroxide concentration and absorbance is shown in Table 2.

TABLE 2

| H$_2$O$_2$ concentration (mmol/l) | OD$_{730}$ Human serum added | OD$_{730}$ Deionized water added |
|---|---|---|
| 0.5 | 0.1790 | 0.1808 |
| 1.0 | 0.3849 | 0.3852 |
| 1.5 | 0.6045 | 0.6052 |
| 2.0 | 0.7990 | 0.8029 |
| 4.0 | 1.6060 | 1.6212 |

As is clear from Table 2, according to the determination method of hydrogen peroxide using the urea derivative of the formula (I) as a color producing component, the measured values are not influenced by the presence of human serum.

EXAMPLE 8

Determination of Uric Acid
[Measuring reagent solution]
In 50 mM PIPES-sodium hydroxide buffer solution (pH 6.4), the following ingredients were dissolved so as to make the concentrations as mentioned below:

| | |
|---|---|
| Compound No. (1) obtained in Example 1 | 0.05 mmol/l |
| Peroxidase | 10 U/ml |
| Uricase | 2 U/ml |
| Ascorbate oxidase | 2 U/ml |

[Sample solution]
A standard solution containing 10 mg/dl of uric acid and 13 samples of human serum were used as samples.
[Measuring method]
To 3 ml of the measuring reagent solution, 20 μl of a sample was added and incubated at 37° C. for 5 minutes. Then, absorbance at 730 nm (OD$_{730}$) was measured.

The uric acid value in human serum was calculated by the following equation:

$$\text{Uric acid (mg/dl)} = \frac{\left(\begin{array}{c}\text{OD}_{730}\text{ of}\\\text{human serum}\end{array}\right) - \left(\begin{array}{c}\text{OD}_{730}\text{ of}\\\text{blank}\end{array}\right)}{\left(\begin{array}{c}\text{OD}_{730}\text{ of}\\\text{standard}\\\text{solution}\end{array}\right) - \left(\begin{array}{c}\text{OD}_{730}\text{ of}\\\text{blank}\end{array}\right)} \times 10$$

Reference Example 1

Determination of Uric Acid

Using the same samples as used in Example 8, the uric acid concentrations were measured by using a commercially available kit for measuring uric acid [Uric acid C-Test Wako, mfd. by Wako Pure Chemical Industries, Ltd.]

Measured results of Example 8 and Reference Example 1 are shown in Table 3.

TABLE 3

| Serum No. | Example 8 (Y) | Reference Example 1 (X) |
|---|---|---|
| 1 | 4.1 (mg/dl) | 4.1 (mg/dl) |
| 2 | 7.9 | 7.5 |
| 3 | 3.0 | 3.0 |
| 4 | 8.2 | 8.2 |
| 5 | 5.0 | 5.2 |
| 6 | 6.7 | 6.9 |
| 7 | 5.9 | 5.8 |
| 8 | 4.8 | 4.8 |

TABLE 3-continued

| Serum No. | Example 8 (Y) | Reference Example 1 (X) |
|---|---|---|
| 9 | 10.5 | 10.4 |
| 10 | 15.5 | 15.5 |
| 11 | 18.0 | 18.1 |
| 12 | 19.9 | 20.3 |
| 13 | 3.4 | 3.3 |
| Average value | 8.7 | 8.7 |

Correlation coefficient: $\gamma = 1.00$
Regression straight line equation: $Y = 0.99 X + 0.11$ As is clear from Table 3, the measured values of uric acid obtained in Example 8 wherein the urea derivative of the formula (I) was used as a color producing agent are well agreed to those obtained by using the commercially available kit.

Example 9

Determination of Uric Acid

[Measuring reagent solution]

In 50 mM PIPES-sodium hydroxide buffer solution (pH 6.4), the following ingredients were dissolved so as to make the concentrations as mentioned below:

| | |
|---|---|
| Compound No. (10) obtained in Example 5 | 0.025 mmol/l |
| Peroxidase | 10 U/ml |
| Uricase | 2 U/ml |
| Ascorbate oxidase | 2 U/ml |

[Sample solution]

A standard solution containing 10 mg/dl of uric acid and 10 samples of human serum were used as samples.

[Measuring method]

To 3 ml of the measuring reagent solution, 20 μl of a sample was added and incubated at 37° C. for 5 minutes. Then, absorbance at 666 nm ($OD_{666}$) was measured.

The uric acid value in human serum was calculated by the following equation:

$$\text{Uric acid (mg/dl)} = \frac{\left(\begin{array}{c}OD_{666} \text{ of} \\ \text{human serum}\end{array}\right) - \left(\begin{array}{c}OD_{666} \text{ of} \\ \text{blank}\end{array}\right)}{\left(\begin{array}{c}OD_{666} \text{ of} \\ \text{standard} \\ \text{solution}\end{array}\right) - \left(\begin{array}{c}OD_{666} \text{ of} \\ \text{blank}\end{array}\right)} \times 10$$

Reference Example 2

Determination of Uric Acid

Using the same samples as used in Example 9, the uric acid concentrations were measured by using a commercially available kit for measuring uric acid [Uric acid C-Test Wako, mfd. by Wako Pure Chemical Industries, Ltd.].

Measured results of Example 9 and Reference Example 2 are shown in Table 4.

TABLE 4

| Serum No. | Example 9 (Y) | Reference Example 2 (X) |
|---|---|---|
| 1 | 3.5 (mg/dl) | 3.5 (mg/dl) |
| 2 | 3.3 | 3.0 |
| 3 | 3.3 | 3.1 |
| 4 | 5.5 | 5.3 |
| 5 | 5.0 | 4.9 |
| 6 | 3.6 | 3.4 |

TABLE 4-continued

| Serum No. | Example 9 (Y) | Reference Example 2 (X) |
|---|---|---|
| 7 | 4.9 | 4.9 |
| 8 | 3.6 | 3.6 |
| 9 | 13.0 | 13.0 |
| 10 | 25.3 | 25.5 |
| Average value | 7.1 | 7.0 |

Correlation coefficient: $\gamma = 1.00$
Regression straight line equation: $Y = 0.98 X + 0.19$ As is clear from Table 4, the measured values of uric acid obtained in Example 9 wherein the urea derivative of the formula (I) was used as a color producing agent are well agreed to those obtained by using the commercially available kit.

Example 10

Determination of Uric Acid

[Measuring reagent solution]

In 50 mM PIPES-sodium hydroxide buffer solution (pH 6.4), the following ingredients were dissolved so as to make the concentration as mentioned below:

| | |
|---|---|
| Compound No. (7) obtained in Example 3 | 0.05 mmol/l |
| Peroxidase | 10 U/ml |
| Uricase | 2 U/ml |
| Ascorbate oxidase | 2 U/ml |

[Sample solution]

A standard solution containing 10 mg/dl of uric acid and 13 human serum samples were used as samples.

[Measuring method]

To 3 ml of the measuring reagent solution, 15 μl of a sample was added and incubated at 37° C. for 5 minutes. Then, absorbance at 740 nm ($OD_{740}$) was measured.

The uric acid value in human serum was calculated by the following equation:

$$\text{Uric acid (mg/dl)} = \frac{\left(\begin{array}{c}OD_{740} \text{ of} \\ \text{human serum}\end{array}\right) - \left(\begin{array}{c}OD_{740} \text{ of} \\ \text{blank}\end{array}\right)}{\left(\begin{array}{c}OD_{740} \text{ of} \\ \text{standard} \\ \text{solution}\end{array}\right) - \left(\begin{array}{c}OD_{740} \text{ of} \\ \text{blank}\end{array}\right)} \times 10$$

Reference Example 3

Determination of Uric Acid

Using the same samples as used in Example 10, the uric acid concentrations were measured by using a commercially available kit for measuring uric acid [Uric acid C-Test Wako, mfd. by Wako Pure Chemical Industries, Ltd.].

Measured results of Example 10 and Reference Example 3 are shown in Table 5.

TABLE 5

| Serum No. | Example 10 (Y) | Reference Example 3 (X) |
|---|---|---|
| 1 | 5.0 (mg/dl) | 5.1 (mg/dl) |
| 2 | 3.9 | 3.8 |
| 3 | 3.2 | 3.3 |
| 4 | 3.2 | 3.3 |
| 5 | 4.0 | 4.1 |
| 6 | 4.5 | 4.5 |
| 7 | 6.5 | 6.5 |

TABLE 5-continued

| Serum No. | Example 10 (Y) | Reference Example 3 (X) |
|---|---|---|
| 8 | 6.8 | 6.7 |
| 9 | 13.5 | 13.3 |
| 10 | 15.3 | 15.1 |
| Average value | 6.6 | 6.6 |

Correlation coefficient: $\gamma = 1.00$
Regression straight line equation: $Y = 1.02 X - 0.14$ As is clear from Table 5, the measured values of uric acid obtained in Example 10 wherein the urea derivative of the formula (I) was used as a color producing agent agree well with those obtained by using the commercially available kit.

EXAMPLE 11

Determination of Non-Esterified Fatty Acid (NEFA) [Measuring reagent solution]

In 50 mM PIPES-sodium hydroxide buffer solution (pH, 6,9), the following ingredients were dissolved so as to make the concentrations mentioned below:

| Compound No (9) obtained in Example 4 | 0.05 mmol/l |
|---|---|
| Peroxidase | 5 U/ml |
| Acyl coenzyme A synthetase (ACS) | 0.1 U/ml |
| Acyl coenzyme A oxidase (ACOD) | 3 U/ml |
| Coenzyme A (CoA) | 0.5 mg/ml |
| Magnesium chloride | 2 mM |
| Emulgen 913 (polyoxy-ethylenenonylphenol ether, mfd. by Kao-Atlas Corporation) | 0.2% |
| Adenosine 5'-triphosphate (ATP) | 3 mg/ml |

[Sample]
A standard solution containing 1 mEq/l of oleic acid and 15 human sera were used as samples.

[Measuring method]
To 3 ml of the measuring reagent solution, 20 µl of a sample was added and incubated at 37° C. for 10 minutes. Then, absorbance at 666 nm (OD$_{666}$) was measured.

The NEFA concentration in human serum was calculated by the following equation:

$$NEFA\ (mEq/l) = \frac{\left(\begin{array}{c}OD_{666}\ of\\ human\ serum\end{array}\right) - \left(\begin{array}{c}OD_{666}\ of\\ blank\end{array}\right)}{\left(\begin{array}{c}OD_{666}\ of\\ standard\\ solution\end{array}\right) - \left(\begin{array}{c}OD_{666}\ of\\ blank\end{array}\right)} \times 1$$

REFERENCE EXAMPLE 4

Determination of NEFA

Using the same samples used in Example 11, the NEFA concentrations were measured by using a commercially available kit for measuring NEFA (NEFA C-Test Wako, mfd. by Wako Pure Chemical Industries, Ltd., containing N-ethylmaleimide as SH reagent in a second measuring reagent solution in order to prevent the influence of CoA on the color developing reaction).

Measured results of Example 11 and Reference Example 4 are shown in Table 6.

TABLE 6

| Sample No. | Example 11 (Y) | Reference Example 4 (X) |
|---|---|---|
| 1 | 0.21 (mEq/l) | 0.21 (mEq/l) |
| 2 | 0.39 | 0.37 |
| 3 | 0.46 | 0.45 |
| 4 | 0.70 | 0.70 |
| 5 | 0.97 | 0.97 |
| 6 | 0.87 | 0.86 |
| 7 | 0.46 | 0.44 |
| 8 | 0.74 | 0.75 |
| 9 | 0.99 | 0.98 |
| 10 | 0.85 | 0.84 |
| 11 | 1.50 | 1.50 |
| 12 | 1.33 | 1.32 |
| 13 | 1.09 | 1.09 |
| 14 | 1.19 | 1.18 |
| 15 | 1.81 | 1.82 |
| Average value | 0.904 | 0.899 |

Correlation coefficient: $\gamma = 0.9998$
Regression straight line equation: $Y = 0.991 X + 0.01$ As is clear from Table 6, the measured values of NEFA obtained in Example 11 wherein the urea derivative of the formula (I) was used as a color producing agent agree well with to those obtained by using the commercially available kit. These results show that when Compound No. (9) is used as a color producing agent for measuring NEFA, it is possible to conduct the measurement without using the SH reagent which was necessary in the prior art method and it is also possible to conduct the measurement by a one liquid method which was impossible according to the prior art method.

As mentioned above, the urea derivatives of the formula (I) have remarkably excellent effects in that trace components in living body samples such as serum, urea, etc. can be measured without being affected by colored interfering substances present in the samples when these urea derivatives are used as a color producing component since the maximum absorption wavelength at the color development is in the longer wavelength side of 650 nm or more, and that these urea derivatives have remarkably good solubility in water or an aqueous solution dissolving a surface active agent, and the stability of the chromogen and the stability of color formed are remarkably excellent.

What is claimed is:

1. A urea derivative represented by the formula:

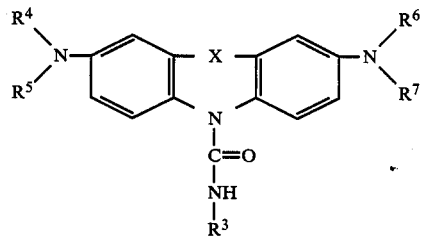

wherein X is S or O; each of $R^4$, $R^5$, $R^6$ and $R^7$ is independently selected from the group consisting of a $C_1$-$C_6$ alkyl group, a carboxy ($C_1$-$C_6$ alkyl) group, a hydroxy ($C_1$-$C_6$ alkyl) group and a ($C_1$-$C_6$ alkoxy) ($C_1$-$C_6$ alkyl) group;

$R^3$ is selected from the group consisting of a carboxy ($C_1$-$C_6$ alkyl) group, a ($C_1$-$C_6$ alkoxy) carbonyl group, a ($C_1$–$C_6$ alkyl) carbonyl group, an arylsulfonyl group, a sulfoaryl group, a carboxyaryl group, and a modified carboxy ($C_1$–$C_6$ alkyl) group wherein the carboxy moiety is in the form of a salt of an alkali metal, the aryl moiety in said arylsulfonyl group, sulfoaryl group and carboxyaryl group being selected from the group consisting of phenyl, tolyl, methoxyphenyl, naphthyl, methylnaphthyl and methoxynaphthyl.

2. A urea derivative according to claim 1, which is represented by the formula:

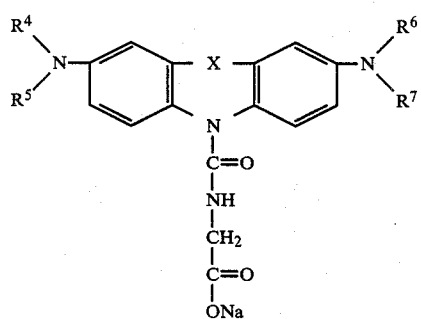

3. A urea derivative according to claim 1, which is represented by the formula:

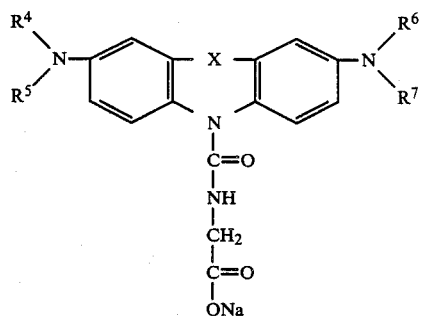

wherein each of $R^4$, $R^5$, $R_6$ and $R_7$ is independently a $C_1$–$C_6$ alkyl group.

4. A urea derivative according to claim 1, which is

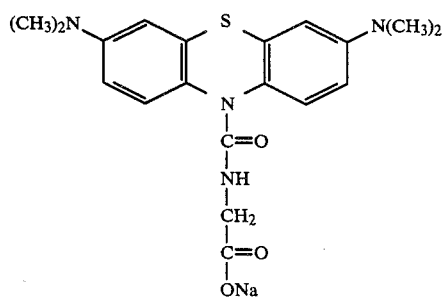

* * * * *